United States Patent [19]

Sasaki et al.

[11] 3,987,113

[45] Oct. 19, 1976

[54] PREPARATION OF 5-METHYL-2-NITROPHENOL

[75] Inventors: Mitsuru Sasaki, Nishinomiya; Katsuji Nodera, Takarazuka; Kunio Mukai, Nishinomiya, all of Japan

[73] Assignee: Sumitomo Chemical Company, Limited, Japan

[22] Filed: June 13, 1975

[21] Appl. No.: 586,755

[52] U.S. Cl. .................. 260/622 R; 260/621 R; 260/505 R; 260/686; 260/463
[51] Int. Cl.² .................................. C07C 79/26
[58] Field of Search ............ 260/622 R, 621 R, 463, 260/621 P, 686, 628, 466 R, 607, 463

[56] References Cited

UNITED STATES PATENTS

| | | | |
|---|---|---|---|
| 2,626,264 | 1/1953 | Brod et al. | 260/463 |
| 2,831,895 | 4/1958 | Stevens et al. | 260/463 |
| 2,985,688 | 5/1961 | Mersch et al. | 260/622 R |
| 3,636,037 | 1/1972 | Donninger et al. | 260/463 |

*Primary Examiner*—James O. Thomas, Jr.
*Assistant Examiner*—W. B. Lone
*Attorney, Agent, or Firm*—Wenderoth, Lind & Ponack

[57] ABSTRACT

A process for preparing 5-methyl-2-nitrophenol from di-m-cresyl carbonate in high yield, by a specific combination of sulfonation, nitration, hydrolysis and steam distillation, is provided.

2 Claims, No Drawings

PREPARATION OF 5-METHYL-2-NITROPHENOL

The present invention relates to a novel process for preparing 5-methyl-2-nitrophenol which is an important intermediate for preparation of agricultural chemicals. More particularly, the present invention relates to a novel process for preparing high-purity 5-methyl-2-nitrophenol characterized by (1) sulfonating di-m-cresyl carbonate with a sulfonating agent, (2) nitrating the resulting sulfonated di-m-cresyl carbonate with a nitrating agent, (3) hydrolyzing the resulting compound to crude nitro-m-cresols, and then (4) steam-distillating said nitro-m-cresols to obtain, as a distillate, 5-methyl-2-nitrophenol.

The objective compound according to the present invention, i.e. 5-methyl-2-nitrophenol, is useful as an intermediate for an excellent herbicide, for example, O-ethyl-O-(5-methyl-2-nitrophenyl)-N-sec.-butylphosphoroamidothioate, which can be obtained by reacting O-ethyl-N-sec.-butyl-thiophosphoroamido chloridate with 5-methyl-2-nitrophenol. Said phosphoroamidothioate is low-toxic and particularly free from delayed neurotoxicity which is characteristic of certain organophosphorus compounds, therefore it is safely usable as a herbicide in the field (Dos-2147873).

A large number of reports on the preparation of substituted phenols have been made prior to the present invention, but none of them gives an economical preparation of 5-methyl-2-nitrophenol.

It is well known that various nitro-isomers are prepared by the nitration of substituted phenols with suitable nitrating agents, and that the direct nitration is limited because of side-reactions and poor yields. For example, direct nitration of m-cresol gives, as a mononitro derivative, a mixture of 3-methyl-2-nitrophenol, 3-methyl-4-nitrophenol and 5-methyl-2-nitrophenol, and the total yield of these isomers is very poor (Liebigs Annalen der Chemie, 217, 51 and 259, 250; Berichte der Deutschen Chemischen Gesellschaft, 40, 4322 and 42, 3098).

As a method other than the above-mentioned ones, there is disclosed in Journal of Chemical Society, 24, 1299 that 5-methyl-2-nitrophenol can be prepared by nitration of sulfonated m-cresol in acetic acid, but description as to the yield and purity is not given therein. The inventors traced the method and confirmed that the total yield was very poor due to the direct nitration as mentioned above and that a large amount of 3-methyl-2-nitrophenol was produced as a by-product.

Furthermore, there is disclosed in Journal of Chemical Society, 1277 (1923) that m-cresol is sulfonated with a fuming sulfuric acid and then the resulting sulfonated m-cresol is nitrated with a mixed acid (nitric acid plus sulfuric acid), but by this method 3-methyl-2-nitrophenol is obtained as a main product and only a small amount of 5-methyl-2-nitrophenol is obtained as a by-product, the total yield being very poor for the reason as mentioned above.

Therefore, the process for preparing high-purity 5-methyl-2-nitrophenol in a high yield is desired at present.

The inventors have studied on the development of an advantageous process for preparing 5-methyl-2-nitrophenol, and found previously that 5-methyl-2-nitrophenol can be obtained in an overall yield of about 60 % from tri-m-cresyl phosphate by subjecting sulfonated tri-m-cresyl phosphate to nitration, followed by hydrolysis, steam-distillating the resulting product to obtain a distillate consisting of 90 % of 5-methyl-2-nitrophenol and 10 % of 3-methyl-2-nitrophenol and then by washing the distillate with a dilute aqueous alkaline solution.

The present inventors have further studied and found the process of the present invention. That is, the merit of the present invention is that carbon dioxide gas produced during hydrolyzing reaction after nitration is easily removed from the reaction system when di-m-cresyl carbonate is used as a starting material for the sulfonation reaction and that pure sulfuric acid can be recovered easily, and further that yield and purity of the objective compound is as good as that of the method using tri-m-cresyl phosphate.

The present reaction proceeds according to the following schema:

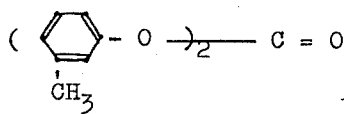

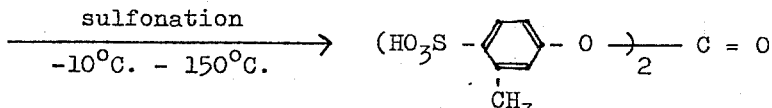

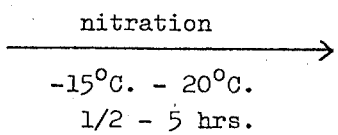

-continued

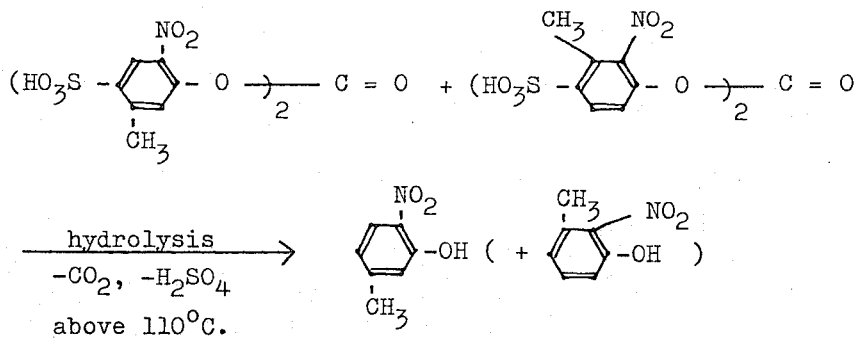

The process according to the present invention will be illustrated in the following in more details.

Di-m-cresyl carbonate used as starting materials is solid materials having melting point of 55° C. Therefore the carbonate can be used as it is in sulfonation at high temperature, but in sulfonation at low temperature the carbonate is preferable to be used by dissolving in a suitable organic solvent, such as carbon tetrachloride, chloroform and ethylene dichloride among which carbon tetrachloride is preferred. These solvents can be removed by azeotropic distillation after nitration reaction.

The sulfonating agents to be used in the present invention include sulfuric acid, various fuming sulfuric acids, chlorosulfonic acid and sulfur trioxide gas, among which sulfuric acid is preferred. The sulfonating reaction condition depends upon the particular sulfonating agent used, and the sulfonating reaction may be carried out within a wide temperature range of −10° C. to 150° C. and within a wide reaction time of ½ to 24 hours.

The nitrating agents to be used in the present invention include nitric acid, various fuming nitric acid, nitric acid plus sulfuric acid (the so-called mixed acid) and acetic acid plus nitric acid, among which the mixed acid is more preferred. The reaction temperatures and times depend upon the particular nitrating agent used, and are generally −15° C. to 20° C. and ½ to 5 hours, respectively.

For the hydrolysis followed by de-sulfonation, it is desirable to use sulfuric acid or conc. hydrochloric acid, among which sulfuric acid is more preferred for recovery and recycle thereof. The temperature and time of the hydrolysis are preferable to be 110° C. to 170° C. and 10 to 20 hours, respectively.

At about 140° C. a mixture of 5-methyl-2-nitrophenol and 3-methyl-2-nitrophenol is distilled out as the azeotropic mixture with distilled water. The mixture is solidified after cooling and filtered up.

When the temperature of hydrolysis is below 140° C., the hydrolysate, a mixture of 5-methyl-2-nitrophenol and 3-methyl-2-nitrophenol is slightly distilled out in the course of hydrolysis. In this case, the hydrolysate is extracted from the reaction mixture with a suitable solvent such as toluene, benzene and carbon tetrachloride. Then, the extract is distilled with steam for the removal of solvent and purification.

According to the process of the present invention, the objective 5-methyl-2-nitrophenol can be obtained in an overall yield of 70 % from m-cresyl carbonate.

The present invention will be illustrated with reference to the following examples, which are given only for the purpose of illustration and not to limit the scope of the invention.

EXAMPLE 1

To 150 g. of conc. sulfuric acid were added 50 g. of di-m-cresyl carbonate in 70 g. of carbon tetrachloride while stirring, during which the temperature rose from 17° C. to 30° C., and the resulting mixture was allowed to stand overnight at room temperature. Then, to the solution was added dropwise at −5° C. to 3° C. a mixed acid of 4 g. of 80 % (w/w) conc. nitric acid and 80 g. of conc. sulfuric acid, and the reaction mixture was kept at 2° C. for 3 hours under stirring. After the reaction was completed, the reaction solution was poured into 500 g. of ice water and then heated to remove carbon tetrachloride. The temperature was further raised and at about 140° C. the mixture of 5-methyl-2-nitrophenol and 3-methyl-2-nitrophenol was distilled out as the azeotropic mixture was distilled water, during which fresh water was added dropwise to supply the water distilled out. When the temperature reached to 165° C., the mixture was cooled as no distillate was obtained. Amount of the distillate thus obtained was 53 g.

The distillate consisted of

| | |
|---|---|
| 5-methyl-2-nitrophenol | 92% (by weight) and |
| 3-methyl-2-nitrophenol | 8% (by weight). |

EXAMPLE 2

To 150 g. of conc. sulfuric acid were gradually added 50 g. of di-m-cresyl carbonate under heating at 80° C. while stirring and the resulting mixture was kept at the same temperature for 2 hours. Then, a mixed acid consisting of 45 g. of 80 % (w/w) of conc. nitric acid and 80 g. of conc. sulfuric acid was added dropwise and the reaction mixture was kept at 2° C. for 3 hours. After the reaction was completed, the reaction solution was poured into 500 g. of ice water, heated up to 120° C. and maintained at the same temperature for 12 hours while stirring. Then, the resulting solution was cooled and extracted with 300 g. of toluene, and further extracted with 300 g. of toluene. The toluene layers were combined and steam-distilled to obtain 51.5 g. of distillate.

The distillate consisted of

| | |
|---|---|
| 5-methyl-2-nitrophenol | 95% (by weight) and |
| 3-methyl-2-nitrophenol | 5% (by weight). |

What we claim is:

1. A process for preparing 5-methyl-2-nitrophenol of the formula:

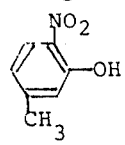

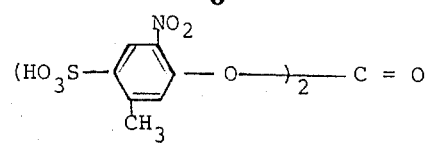

which comprises treating di-m-cresyl carbonate of the formula,

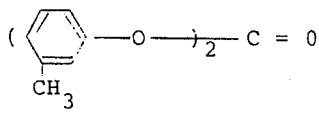

with a sulfonating agent, nitrating the compound thus obtained of the formula,

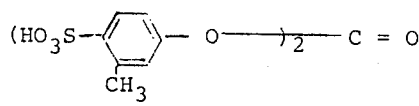

with a nitrating agent, hydrolyzing the compound thus obtained of the formula, and steam-distillating crude nitro-m-cresols thus obtained;

said sulfonating reaction being carried out at −10° C to 150° C in the presence of a sulfonating agent selected from a group consisting of sulfuric acid, fuming sulfuric acid, chlorosulfonic acid and sulfur trioxide;

said nitrating reaction being carried out at −15° C to 20° C in the presence of a nitrating agent selected from the group consisting of nitric acid, fuming nitric acid, a mixture of nitric acid plus sulfuric acid and a mixture of acetic acid plus nitric acid;

said hydrolysis reaction being carried out at 110° C to 170° C in the presence of a sulfuric acid or concentrated hydrochloric acid.

2. The process according to claim 1, wherein each reaction is carried out in the presence or absence of a solvent.

* * * * *